United States Patent
Kimura et al.

(10) Patent No.: US 6,416,546 B1
(45) Date of Patent: Jul. 9, 2002

(54) MEDICAL DEVICE AND PRODUCTION METHOD THEREOF

(75) Inventors: Takashi Kimura; Kunihiko Takagi, both of Kyoto (JP)

(73) Assignee: Unitika Ltd., Hyogo (JP)

(*) Notice: Subject to any disclaimer, the term of this patent is extended or adjusted under 35 U.S.C. 154(b) by 0 days.

(21) Appl. No.: 09/627,794

(22) Filed: Jul. 27, 2000

Related U.S. Application Data

(63) Continuation-in-part of application No. 09/089,390, filed on Jun. 3, 1998, now abandoned.

(30) Foreign Application Priority Data

Jun. 4, 1997 (JP) ................................ 9-146220

(51) Int. Cl.[7] .................................................. A61F 2/06
(52) U.S. Cl. ..................................................... 623/1.46
(58) Field of Search ............................. 623/1.46, 23.59; 427/2.24, 2.25, 2.3, 2.31

(56) References Cited

U.S. PATENT DOCUMENTS

| | | | |
|---|---|---|---|
| 3,067,099 A | * 12/1962 | McCormick et al. | |
| 4,378,435 A | 3/1983 | Takagi et al. | |
| 4,539,234 A | 9/1985 | Sakamoto et al. | |
| 5,217,493 A | 6/1993 | Raad et al. | |
| 5,322,659 A | 6/1994 | Walder et al. | |

FOREIGN PATENT DOCUMENTS

| | | |
|---|---|---|
| EP | 0 470 443 A2 | 2/1992 |
| JP | 50-139174 | 11/1975 |
| JP | 53-15913 | 5/1978 |
| JP | 56-34203 | 8/1981 |
| JP | 62-14273 | 4/1987 |
| JP | 2-25625 | 6/1990 |
| JP | 7-501470 | 2/1995 |
| JP | 10-328293 | 12/1998 |
| JP | 10-328294 | 12/1998 |

OTHER PUBLICATIONS

Abstract of No. 11 Nippon *geka kannsensyo kennkyukai*, Subject No. 28, p. 147 (published Nov. 30, 1998).
Nippon *geka kannsensyo kennkyukai*, 11, 106–110, 1999.
European Search Report for EP 98 11 0173.

* cited by examiner

Primary Examiner—Corrine McDermott
Assistant Examiner—Hieu Phan
(74) Attorney, Agent, or Firm—Sughrue Mion, PLLC

(57) ABSTRACT

A medical device and production method therefor which can retain antimicrobial activity for a prolonged period of time under physiological indwelling conditions and also having a physiologically active function. The production method is independent of the kind of base material selected for the medical device. The antimicrobial medical device having physiological activity comprises a cross-linked coating film constituting a high molecular weight substance having acid anhydride groups formed on a surface of a base material. The cross-linked coating film is formed by reacting preferably from 0.5 to 10 mol % of the acid anhydride groups contained in the high molecular weight substance with a compound having two or more active hydrogen atoms in one molecule. Also, a physiologically active substance and an antimicrobial substance are bonded to the cross-linked coating film.

20 Claims, 1 Drawing Sheet

MEDICAL DEVICE AND PRODUCTION METHOD THEREOF

CROSS-REFERENCE TO RELATED APPLICATIONS

This is a continuation-in-part of application Ser. No. 09/089,390, filed Jun. 3, 1998 now abandoned.

FIELD OF THE INVENTION

This invention relates to a medical device which has physiological activity and can maintain its antimicrobial activity for a prolonged period of time under physiological conditions, and to a method for producing the medical device.

BACKGROUND OF THE INVENTION

Proposals have been made to develop medical materials having various functions by attaching to the surface thereof enzymes, polysaccharides, coenzymes, enzyme inhibitors, hormones, antigens, antibodies and the like physiologically active substances. For example, JP-A-50-139174 (the term "JP-A" as used herein means an "unexamined published Japanese patent application") discloses a method in which a high molecular weight substance having hydroxyl groups is reacted with an aminoaldehyde, aminoacetal or the like to introduce amino groups into the high molecular weight substance which is then reacted with heparin. Also, JP-B-53-15913 (the term "JP-B" as used herein means an "examined Japanese patent publication") discloses a method for imparting fibrinolytic activity in which a fibrinolytic enzyme is linked to the surface of a polyamide. In addition, Japanese Patent No. 1406830 discloses a method in which enzyme activity is added to the surface of a solid material.

On the other hand, cases have been increasing in recent years in which a treatment or diagnosis is carried out by percutaneously inserting and indwelling a catheter or the like medical device into the living body. However, such procedures also cause a serious problem of inducing infectious diseases mediated by the catheter and the like medical devices. For example, a vessel catheter or a ureteral catheter is indwelt in the living body for a prolonged period of time in many cases, and bacteria invade through these catheters and frequently cause sepsis, urethritis, cystitis, pyelitis and the like symptoms. Because of this, washing of the inserting part of each medical device or injection of a germicide is carried out as a means for preventing infectious diseases caused by a catheter and the like medical devices. However, not only is such handling complex, but also the handling itself becomes a new source of infection.

Although the preventive administration of antibiotics and chemotherapeutic drugs is also carried out, it is said that unplanned chemotherapy is harmful because of the problems of inducing side effects and increasing the generation frequency of resistant strains. Also, these antibiotics and chemotherapeutic drugs are meant to be topically applied. With regard to the topical use of antibiotics and chemotherapeutic drugs, JP-B-2-25625 discloses a ureteral catheter having the ability to prevent urinary tract infection, in which antibiotics are linked through an ionic bonding to a ureteral catheter made of an olefinic polymer, a diene polymer or a silicon polymer as a raw material. JP-B-56-34203 discloses a method for producing an antimicrobial material in which a high molecular weight substance having acidic groups is allowed to react with bis-(p-chlorophenyldiguanido)-hexane or a salt thereof. Additionally, JP-W-7-501470 (the term "JP-W" as used herein means an "published Japanese national phase international patent application") discloses antimicrobial medical articles coated with antimicrobial substances.

In addition, an antimicrobial antithrombogenic composition which contains a fat-solubilized mucopolysaccharide of an ionic complex of a mucopolysaccharide with a quaternary ammonium or a quaternary phosphonium has also been disclosed (JP-A-10-295799, JP-A-10-179724),but it has a disadvantage in that the quaternary ammonium or quaternary phosphonium as the antimicrobial component of this case has relatively weak antimicrobial activity.

On the contrary, JP-A-10-328293 shows that a physiologically active substance and an antimicrobial activity can be added simultaneously and relatively easily independent of the base material which constitutes a medical device. When this method is used, a medical device having high degree functions can be easily obtained by binding a combination of an antimicrobial substance having relatively strong antimicrobial activity and useful substances having various physiological activities on a surface of the base material of the medical device.

Depending on the medical devices to be used in the clinical field, there are cases in which persistence of functions is required for a relatively prolonged period of time regarding their use period, and antimicrobial activity is one such function. However, in the case of the medical device and its production method disclosed in JP-A-10-328293, an antimicrobial substance is gradually released from the base material surface during use of the medical device, and the duration of antimicrobial property therefore is not sufficient in some cases depending on the kinds of the antimicrobial substance. Thus, it is necessary to obtain persistence of the antimicrobial property for more prolonged period of time.

The invention contemplates resolving these problems and thereby providing a medical device which has a physiological activity and which can maintain its antimicrobial activity stably for a prolonged period of time under physiological conditions, and a method for producing the medical device.

SUMMARY OF THE INVENTION

It is therefore an object of the present invention to solve the aforementioned problems of the prior art, and to thereby provide a medical device which simultaneously exhibits both excellent physiological and antimicrobial activity and a method for producing the same.

For the purpose of achieving the above object, the present inventors have conducted extensive studies and found as a result of their efforts, that a medical device which maintains its antimicrobial activity for a prolonged period of time even by indwelling under physiological conditions, can be obtained by reacting preferably from 0.5 to 10 mol % of acid anhydride groups in a high molecular weight substance having acid anhydride groups with a compound having two or more active hydrogen atoms in one molecule on a surface of the medical device, thereby forming and fixing a cross-linked coating film on the surface, and subsequently bonding a physiologically active substance and an antimicrobial substance to acid anhydride groups or carboxylate groups in the high molecular weight substance to thereby achieve the present invention.

Accordingly, a first embodiment of the invention relates to an antimicrobial medical device having physiological activity, which comprises a cross-linked coating film constituting a high molecular weight substance having acid anhydride groups formed on a surface of a base material, said cross-linked coating film is formed by reacting preferably from 0.5 to 10 mol % of the acid anhydride groups contained in the high molecular weight substance with a compound having two or more active hydrogen atoms in one molecule, and wherein a physiologically active substance and an antimicrobial substance are bonded to the cross-linked coating film.

Also, a second embodiment of the invention relates to a method for producing an antimicrobial medical device having physiological activity, which comprises forming a cross-linked coating film constituting a high molecular weight substance having acid anhydride groups on a surface of a base material of the medical device, by reacting preferably from 0.5 to 10 mol % of acid anhydride groups contained in the high molecular weight substance with a compound having two or more active hydrogen atoms in one molecule, and subsequently bonding a physiologically active substance and an antimicrobial substance to the cross-linked coating film.

According to the present invention, a medical device having functions of both physiological activity and antimicrobial activity can be obtained by a simple and easy method.

Other objects and advantages of the present invention will become apparent in view of the followed detailed description and working examples.

DETAILED DESCRIPTION OF THE INVENTION

Figure 1:
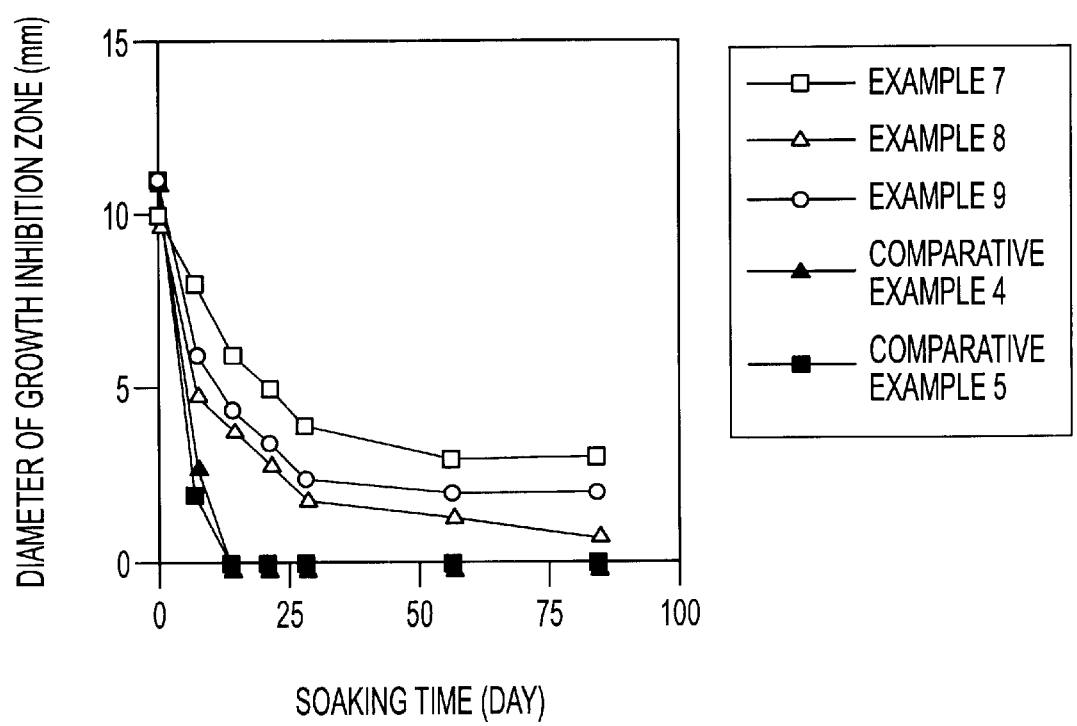
FIG. 1 is a graph showing periodical plotting of the diameter of growth inhibition zone when various antimicrobial antithrombogenic catheter tubes were soaked in physiological saline and shaken at 37° C.

The medical device according to the present invention, although not particularly limited, is a device which is mainly used for indwelling in the living body, and illustrative examples thereof include an IVH catheter, a thermodilution catheter, an angiography catheter, a vasodilation-catheter, an artificial blood vessel, a shunt tube, a canula, a dilator, an indwelling needle, a guide wire, various sensors for use in the measurement of blood flow and blood gas concentration and the like medical devices which are inserted into or indwelt in blood vessels; a ureteral catheter and the like medical devices which are inserted into or indwelt in the urinary tract or ureter; a tracheotomy tube, an endotracheal tube and the like medical devices which are inserted into or indwelt in the trachea; and a nasal feeding tube, a nutrition catheter, a feeding gastric tube and the like medical devices which are inserted or indwelt orally or transnasally; as well as an artificial kidney, an artificial heart, an artificial valve, an artificial lung and the like medical devices.

Although not particularly limited, the base material which constitutes the medical device preferably comprises a high molecular weight material such as polyurethane, polyamide, polyester, polyvinyl chloride, polyethylene, polypropylene, polystyrene, polyacrylic acid ester, polymethacrylic acid ester, polycarbonate, polyacrylonitrile, polyacrylamide, polyacrylic acid, polymethacrylic acid, polyvinyl alcohol, polymaleic anhydride, polyethyleneimine, cellulose, natural rubber or the like organic substance or silicone resin, glass, asbestos, mica, activated carbon, polyphosphazene or the like inorganic substance. In the case of a medical device composed of a metal or the like material other than a high molecular weight material, a cross-linked coating film can be formed directly on its surface, but it is effective and desirable to first coat the base material with the aforementioned high molecular weight material and to then form a cross-linked coating film on the surface of the high molecular weight material.

According to the medical device of the present invention, a cross-linked coating film is formed on the surface of the base material, and a physiologically active substance and an antimicrobial substance are bonded to the thus formed cross-linked coating film. This cross-linked coating film can be obtained by allowing a high molecular weight substance having acid anhydride groups to react with a compound having two or more active hydrogen atoms in accordance with a method which will be described below.

The high molecular weight substance having acid anhydride groups for use in the present invention is a polymer or copolymer which contains at least ten monomer units, each having an acid anhydride group, in one molecule, and contains preferably 10 to 10,000, more preferably 100 to 1000 acid anhydride groups per one molecule. Illustrative examples thereof include maleic anhydride-ethylene copolymer, maleic anhydride-styrene copolymer, maleic anhydride-methyl vinyl ether copolymer and the like maleic anhydride polymers, polyacrylic anhydride, acrylic anhydride-styrene copolymer and the like acrylic anhydride polymers, and polymethacrylic anhydride, methacrylic anhydride-styrene copolymer and the like methacrylic anhydride polymers. The weight-average molecular weight of the high molecular weight substance having acid anhydride groups is not particularly limited, but is generally 500 or more, preferably 750 or more, more preferably 1,000 or more.

The compound having two or more active hydrogen atoms for use in the present invention is a compound having at least two groups selected from a hydroxyl group, an amino group, a thiol group and the like active hydrogen groups in one molecule, and illustrative examples thereof include a polyol, a polyanine and the like compounds.

The polyol is a low molecular weight or high molecular weight compound having at least two hydroxyl groups in one molecule, and illustrative examples thereof include ethylene glycol, propylene glycol, butylene glycol, glycerol, pentaerythritol, sorbitol, diglycerol, diethylene glycol, triethylene glycol, tetraethylene glycol, pentaethylene glycol, dipropylene glycol, tripropylene glycol, polyethylene glycol, polypropylene glycol, polybutylene glycol and the like, of which a polyalkylene glycol is particularly preferred.

The polyamine is a low molecular weight or high molecular weight compound having at least two amino groups in one molecule, and illustrative examples thereof include ethylenediamine, propylenediamine, hexamethylenediamine, poly (oxyethylene)diamine, poly (oxypropylene)diamine and the like diamines, polyvinylamine, aminoacetalized polyvinyl alcohol, polyethyleneimine and a reaction product of a diamine with epichlorohydrin.

According to the medical device of the present invention, a physiologically active substance is linked via covalent bonds to unreacted acid anhydride groups which are present in the cross-linked coating film, and an antimicrobial substance is linked via ionic bonds to carboxyl groups formed by the hydrolysis of the acid anhydride groups.

The physiologically active substance according to the present invention is a substance which has a physiological activity other than antimicrobial activity, and it must have amino group in its structure. Illustrative examples of such a substance include drugs, coenzymes, antibodies, receptors, antigens, complements, hormones, enzymes such as deoxyribonuclease, a blood proteolytic enzyme and the like, enzyme substrates, enzyme inhibitors and blood proteins such as albumin, globulin, ceruloplasmin, transferrin, cycloglobulin, haptoglobulin, hemopexin, conglutinin and the like, of which streptokinase, urokinase, plasmin, brinolase, tissue plasminogen activator and the like fibrinolytic enzymes are particularly preferred.

The antimicrobial substance for use in the present invention is preferably a basic antimicrobial substance, and illustrative examples thereof include amoxicillin, ampicillin, ciclacillin, sultamicillin tosilate, talampicillin hydrochloride, bacampicillin hydrochloride, hetacillin potassium, lenampicillin hydrochloride, pivmecillinam hydrochloride, aspoxicillin and the like penicillin antibacterial drugs; cefaclor, cefatrizine propylene glycol, cefadroxil, cefalexin, cefaloglycin, cefradine, cefroxadine, cefazolin sodium, cefapirin sodium, cefaloridine, ceftezole sodium, cefotiam hydrochloride, cefamandole sodium, cefametazole sodium, cefasulodin sodium, cefmenoxime hydrochloride, cefotaxime sodium, cefotetan, cefoperazone sodium, ceftazidime, ceftizoxime sodium, ceftriaxone sodium, cefpimizole sodium, cefpiramide sodium, cefbuperazone sodium, latamoxef sodium, cefixime, cefteram pivoxyl, cefminox sodium, cefuzonam sodium and the like cephalosporin antibacterial drugs; gentamicin sulfate, netilmicin sulfate, tobramycin, amikacin sulfate, streptomycin sulfate, fradiomycin sulfate, bekanamycin sulfate, paromomycin sulfate, ribostamycin sulfate, kanamycin sulfate, dibekacin sulfate, sisomicin sulfate, micronomicin sulfate, astromicin sulfate and the like aminoglycoside antibacterial drugs; colistin sulfate, polymyxin B sulfate and the like polypeptide antibacterial drugs; oxytetracycline, tetracycline, demethylchlor tetracycline, doxycycline hydrochloride, minocycline hydrochloride, rolitetracycline and the like tetracycline antibacterial drugs; lincomycin hydrochloride, clindamycin hydrochloride, clindamycin palmitate hydrochloride, clindamycin phosphate and the like lincomycin antibacterial drugs; erythromycin, erythromycin estolate, erythromycin ethylsuccinate, oleandomycin phosphate, triacetyloleandomycin, kitasamycin, acetylkitasamrycin, acetylspiramycin, josamycin, josamycin propionate, midecamycin, midecamycin acetate, rokitamycin and the like macrolide antibacterial drugs; thiamphenicol aminoacetate hydrochloride and the like chloramphenicol antibacterial drugs; cycloserine, rifampicin, capreomycin sulfate, enviomycin sulfate and the like antituberculous drugs; nystatin, amphotericin B and the like antimycotic drugs; vancomycin hydrochloride and the like glycopeptide antibacterial drugs; and aztreonam, spectinomycin hydrochloride, imipenem-cilastatin sodium and the like antibiotics.

Also useful as the antimicrobial substance of the present invention includes sulfisomidine, sulfamethizole, sulfamethoxazole, acetylsulfamethoxazole, sulfamonomethoxine, sulfadimethoxine, sulfaphenazole, sulfamethopyrazine, salazosulfapyridine and the like sulfa drugs; calcium p-aminosalicylate, calcium alumino-p-aminosalicylate, isoniazid, isoniazid sodium methanesulfonate, isoniazid sodium glucuronate, isoniazid calcium pyruvate, pyrazinamide, ethionamide, protionamide, ethambutol hydrochloride and the like antituberculous agents; glucosulfone sodium, diaphenylsulfone, thiazosulfone, and the like antileprotics; nitrofurantoin and the like furan preparations; nalidixic acid, piromidic acid, pipemidic acid trihydrate, cinoxacin, enoxacin, ofloxacin, norfloxacin and the like pyridone carboxylic acid preparations; flucytosine, miconazole and the like antimycotic agents; aciclovir, vidarabine and the like antiviral agents; and trimethoprim and the like chemotherapeutic agents having basic functional groups. In addition, chlorhexidine gluconate, benzalkonium chloride and the like dermatologic germicidal disinfectants having basic functional groups can also be used as the antimicrobial substance of the present invention. Although these antimicrobial substances may exist in various salt forms in addition to their free forms, any one of these forms can be used as the antimicrobial substance of the present invention as a matter of course. These antimicrobial substances may be used alone or as a mixture thereof.

Based on the construction described above, the medical device of the present invention simultaneously expresses both physiological and antimicrobial activities.

Next, the method for producing a medical device as a second aspect of the present invention is described below.

Firstly, a cross-linked coating film is formed on the surface of the medical device base material as described above, by allowing the aforementioned high molecular weight substance having acid anhydride groups to react with the aforementioned compound having two or more active hydrogen atoms. In order to effect this reaction, the surface of the base material of a medical device is contacted with a solution in which the high molecular weight substance having acid anhydride groups and the compound having two or more active hydrogen atoms are dissolved.

Examples of the solvent for use in dissolving the high molecular weight substance having acid anhydride groups and the compound having two or more active hydrogen atoms include dioxane, tetrahydrofuran, ethyl acetate, acetone, methyl ethyl ketone, chloroform, nitromethane, benzene, toluene, xylene, dimethylformamide, dimethylacetamide, dimethyl sulfoxide and the like solvents.

The high molecular weight substance having acid anhydride groups is dissolved in the above described solvent in an amount of 0.1% by weight or more, preferably from 0.2 to 10% by weight, more preferably from 0.5 to 5.0% by weight. A polyol, polyamine or the like compound having two or more active hydrogen atoms is further dissolved therein in an amount of 0.001% by weight or more, preferably from 0.005 to 10.0% by weight, more preferably from 0.01 to 5.0% by weight. If the amount of each of these materials dissolved in the solvent is too low, then this would reduce the strength of the coating film thus formed, and if too high, would cause unevenness in the thickness of the coating film.

Regarding the compound having two or more active hydrogen atoms in one molecule, when its concentration in the solvent described above is high, it reacts with a large number of acid anhydride groups in the high molecular weight substance, so that flexibility of the cross-linked coating film thereby formed on a surface of the base material is reduced. Since the ability of such a cross-linked coating film having reduced flexibility to adhere to a base material is reduced when used as a medical device, as a result, physiological activity and antimicrobial activity are lost from the base material.

On the other hand, when the concentration of the compound in the solvent is low, the bonded physiologically active substance and antimicrobial substance cannot be sufficiently retained, and these substances are quickly washed away under physiological conditions. As a result, the base material surface cannot maintain its physiological activity and antimicrobial activity for a prolonged period of time.

Accordingly, in order to effect formation of a cross-linked coating film, it is necessary to use the compound having two or more active hydrogen atoms in one molecule, in such a concentration that from 0.5 to 10 mol % of acid anhydride groups in the high molecular weight substance react with the compound having active hydrogen atoms. In addition, the cross-linked coating film obtained within such a concentration range can bind a sufficient amount of the physiologically active substance and also can form an appropriate space in which the antimicrobial substance can be retained for a prolonged period of time under physiological conditions.

The method for contacting the thus prepared solution with the surface of a base material is not particularly limited. Examples thereof include a method in which a medical device is soaked in the aforementioned solution, a method in which the solution is sprayed on the surface of the base material and a method in which the solution is coated on the surface of the base material. Of these, the method in which a medical device is soaked in the solution is particularly preferred because of its good reproducibility.

In the soaking method, the soaking time may be preferably from 10 seconds to 24 hours, more preferably from 30 seconds to 2 hours.

After contacting the solution with the surface of a base material, a cross-linked coating film is formed by allowing the base material to stand at a temperature of preferably from −50 to 180° C., more preferably from 0 to 150° C., for a period of from 5 minutes 72 hours, preferably from 10 minutes to 48 hours, more preferably from 30 minutes to 24 hours.

Next, a physiologically active substance and an antimicrobial substance are linked to the medical device on which a cross-linked coating film has been formed.

With regard to the method for linking a physiologically active substance to the cross-linked coating film, the solution containing the aforementioned physiologically active substance may be sprayed or coated on the medical device of interest having a cross-linked coating film formed thereon. In the case of a tubular medical device such as a catheter, a solution containing a physiologically active substance having amino groups may be circulated in the tube, but a method in which a medical device is soaked in a solution containing a physiologically active substance is most simple and easy.

The solvent for use in this case is not particularly limited, with the proviso that it can dissolve the physiologically active substance and is free from amino groups. However, it is desirable to use an aqueous solution which is adjusted to a pH value of from 3 to 10 when a fibrinolytic enzyme is linked to the coating film. The amount of the physiologically active substance to be dissolved in this solution varies depending, for example, on the type of each physiologically active substance and the shape of each medical device. In the case of a fibrinolytic enzyme, the solution may be prepared such that its concentration per unit area of a medical device is 10 to 1,000 units/cm$^2$. Preferably, the soaking may be carried out for a period of from 1 to 48 hours at a temperature of from 0 to 80° C.

With regard to the ionic bonding of an antimicrobial substance, the solution containing the aforementioned antimicrobial substance may be sprayed or coated or, in the case of a tubular medical device such as a catheter, a solution containing an antimicrobial substance may be circulated in the tube. However, a method in which a medical device is soaked in a solution of an antimicrobial substance is the most simple and easy method.

The solvent for use in this case is not particularly limited, with the proviso that it can dissolve the antimicrobial substance, but water is most preferred. Preferably, the antimicrobial substance is used in a concentration of from 0.01 to 10% by weight, and the soaking may be carried out for a period of from 5 minutes to 48 hours at a temperature of from 0 to 80° C.

In carrying out ionic bonding of an antimicrobial substance, it is efficient and therefore desirable to adjust the pH value of the antimicrobial substance solution within a specified range. That is, the solution is maintained under a weakly acidic to alkaline condition, illustratively at a pH value of from 4 to 14. In order to adjust the pH value, an acid or alkali may be added dropwise, or a buffer solution having an appropriate concentration may be used. The antimicrobial substance thus linked via ionic bonding to the cross-linked coating film of a medical device is maintained on the coating film for a prolonged period of time and keeps its antimicrobial activity during use.

As described above, a physiologically active substance and an antimicrobial substance may be linked in order, but it is possible as a matter of course to simultaneously link the physiologically active substance and the antimicrobial substance to the cross-linked coating film. With regard to a method for simultaneous linking, a solution containing the physiologically active substance and the antimicrobial substance may be sprayed or coated on the medical device of interest having formed thereon a cross-linked coating film. In the case of a tubular medical device such as a catheter, the solution may be circulated in the tube, but a method in which a medical device is soaked in the solution is the most simple and easy method. Preferably, the soaking may be carried out for a period of from 1 to 48 hours at a temperature of from 0 to 80° C.

Because these methods for carrying out ionic bonding of an antimicrobial substance to the medical device are markedly easy and simple, they can be practiced easily by doctors, pharmacists, nurses and the like persons engaged in medical treatments at hospitals, drugstores and the like places where health control is practiced. In that case, doctors, pharmacists, nurses and the like persons engaged in medical treatments can prepare a made-to-order medical device in a hospital by selecting an appropriate antimicrobial substance in response to the actual circumstances of the hospital, such as the kinds of infectious bacteria and the like. Furthermore, depending on each type of disease, such persons may carry out ionic bonding of the thus selected antimicrobial substance to a physiologically active substance-linked medical device.

EXAMPLES

Examples of the present invention are given below by way of illustration and not by way of limitation.

Reference Example 1
(Test of Antimicrobial Activity)

The antimicrobial activity of each sample was tested by the following diffusion method.

In the case of a catheter tube, it was cut into a length of 5 mm, and in the case of a film, it was punched out into a disc of 5 mm in diameter, and used as respective samples. Thereafter, the sample was placed on an agar plate medium on which cells of *Staphylococcus aureus* ATCC 29523 had been spread. The resulting plate was incubated at 37° C. for 24 hours, and then the size of the growth inhibition zone formed around the sample was measured. This was used as an index of antimicrobial activity ("Bioassay of Physiologically Active Substances", issued by Kodan-sha, p. 18).

Reference Example 2
(Test of Fibrinolytic Activity)

The fibrinolytic activity of each sample was tested by the method of Kanai et al. ("A Manual of Clinical Inspection Methods", revised 27th edition, issued by Kanehara Shuppan, VI-100). Namely, a sample was placed on a fibrin plate and incubated at 37° C. for 24 hours, and then lysis of the fibrin membrane around the disc was observed.

Reference Example 3
(Test of Urokinase Activity)

The urokinase activity of each sample was tested by a synthetic substrate method (Morita et al., *J. Biochem.*, 82, 1495 (1977)).

Namely, a catheter tube having a length of 1 cm was soaked in Tris-HCl buffer (pH 8.0) containing Glt-Gly-Arg-MCA (mfd. by Peptide Research Institute) and a reaction for a period of 10 minutes was carried out at 37° C. After completing the reaction, the activity of urokinase covalently bonded to the sample were obtained by measuring the fluorescence intensity (Ex., 380 nm; Em., 460 nm) of the reaction solution.

Example 1

Firstly, 5% by weight of a maleic anhydride-methyl vinyl ether copolymer having a molecular weight of about 67,000 (mfd. by I. S. P.) and 0.1% by weight of polyethylene glycol having an average molecular weight of 3,000 (mfd. by Maruzen Pharmaceutical) were dissolved in acetone. Next, a catheter tube made of nylon 6 (5.6 mm in inner diameter and 8.0 mm in outer diameter, mfd. by UNITIKA) was soaked in the acetone solution for 1 hour at room temperature and then removed from the acetone solution and air-dried. The catheter tube was then heated at 90° C. for 3 hours under reduced pressure to form a cross-linked coating film thereon. The catheter tube on which a cross-linked coating film had been formed was soaked in an aqueous solution containing 0.1 mg/ml of streptokinase (mfd. by Nakalai Tesque) and 1 mg/ml of kanamycin sulfate (mfd. by Wako Pure Chemical Industries) for 24 hours and then dried, to thereby obtain a medical device of the present invention having both fibrinolytic and antimicrobial activities.

The antimicrobial activity and fibrinolytic activity of this medical device were evaluated by the methods of Reference Examples 1 and 2. It was confirmed that the device possessed both of these functions.

Example 2

Firstly, a catheter tube having an inner diameter of 1.8 mm and an outer diameter of 2.2 mm was obtained by subjecting polyurethane (Pellethane, mfd. by Dow Chemical) to extrusion molding at 180° C.

Next, 5% by weight of a maleic anhydride-methyl vinyl ether copolymer having a molecular weight of about 67,000 (mfd. by I. S. P.) and 0.1% by weight of polyethylene glycol having an average molecular weight of 3,000 (mfd. by Maruzen Pharmaceutical) were dissolved in acetone. The above prepared polyurethane catheter tube was soaked in the acetone solution for 1 minute at room temperature and then heated at 70° C. for 24 hours to form a cross-linked coating film. The catheter tube having thereon the cross-linked coating film was then soaked in physiological saline containing 600 units/ml of urokinase (mfd. by The Green Cross Corporation) for 24 hours at 7° C. and then dried. Thereafter, the thus treated catheter tube was again soaked in an aqueous solution containing 1 mg/nl of vancomycin hydrochloride (mfd. by Nakalai Tesque) for 1 hour at room temperature and then dried, to thereby obtain a medical device having both urokinase activity and antimicrobial activity.

The antimicrobial activity and urokinase activity of the thus obtained catheter tube were evaluated by the methods of Reference Examples 1 and 3. It was confirmed that the tube possessed both of these activities.

Comparative Example 1

Following the procedure of Example 2, a catheter tube to which urokinase was linked but vancomycin hydrochloride was not linked was prepared for the sake of comparison, and was found to have a urokinase activity similar to that of Example 2. This result suggests that the urokinase activity is not affected by the presence or absence of bound vancomycin hydrochloride.

Comparative Examples 2 and 3

Following the procedures of Comparative Example 2, a catheter tube to which urokinase was not linked but vancomycin hydrochloride was linked was prepared for comparison (Comparative Example 2). Also, another catheter tube was prepared by repeating the procedure of Example 2 except that polyethylene glycol was not used (Comparative Example 3). Each of the catheter tubes of Example 2 and Comparative Examples 2 and 3 was soaked in a 1 M sodium chloride aqueous solution, and the amount of vancomycin released in the supernatant was measured by liquid chromatography (column: Cosmosil 5C18-MS mfd. by Nakalai Tesque, 10% acetonitrile, detection: 254 nm). As a result, the adsorbed amount of vancomycin was 121 $\mu g/cm^2$ in the tube of Example 2 and 120 $\mu g/cm^2$ in the tube of Comparative Example 2, but no vancomycin adsorption was observed in the tube of Comparative Example 3. Based on these results, it was found that the amount of adsorbed vancomycin is hardly affected by the presence or absence of bound urokinase, and that adsorption of vancomycin is due to the addition of a cross-linking agent.

Examples 3 to 6

Firstly, a catheter tube having an inner diameter of 5.6 mm and an outer diameter of 8.0 mm was obtained by subjecting polyethylene terephthalate (mfd. by UNITIKA) to extrusion molding at 180° C.

Next, 5% by weight of a maleic anhydride-methyl vinyl ether copolymer having a molecular weight of about 67,000 (mfd. by I. S. P.) and 0.1% by weight of poly(oxyethylene) diamine having an average molecular weight of 3,000 (mfd. by Sanyo Kasei Kogyo) were dissolved in acetone. The above obtained catheter tube was soaked in the acetone solution for 1 minute at room temperature and then air-dried and allowed to stand at room temperature to form a cross-linked coating film thereon. The catheter tube having a coating film thereon was soaked in physiological saline containing 600 international units/ml of urokinase (mfd. by The Green Cross Corporation) for 24 hours at 7° C. and then dried. Thereafter, the thus treated catheter tube was again soaked in an aqueous solution containing 1 mg/ml of cefazolin sodium (Example 3), amikacin sulfate (Example 4), minocycline hydrochloride (Example 5) or rifampicin (Example 6) for 1 hour at room temperature and then dried, to thereby obtain four different medical devices of the present invention having both urokinase activity and antimicrobial activity.

The antimicrobial and urokinase activities of the thus obtained catheter tubes were evaluated by the methods of Reference Examples 1 and 3. It was confirmed that these four tubes possessed the respective antimicrobial and urokinase activities.

Example 7

A polyurethane catheter tube of 1.75 mm in inner diameter and 2.20 mm in outer diameter was soaked in an acetone solution prepared by dissolving 2% by weight of a maleic anhydride-methyl vinyl ether copolymer having a molecular weight of about 67,000 (mfd. by I. S. P.; 429 moles maleic anhydride groups per 1 mole of the copolymer) and 1.02% by weight of polyethylene glycol having a molecular weight of 4,000 (mfd. by Maruzen Pharmaceutical; 2 moles hydroxy groups per 1 mole of the copolymer) (terminal hydroxyl groups of polyethylene glycol: 4.0 mol % based on acid anhydride groups in the maleic anhydride-methyl vinyl ether copolymer), for 10 minutes at room temperature and then removed from the solution. The treated catheter tube was air-dried and then heated at 70° C. for 24 hours. This was then soaked in a phosphate buffer solution (pH 6.0) containing 1,000 units/ml of urokinase (mfd. by Yoshitomi Pharmaceutical) at 20° C. for 24 hours to fix urokinase on the catheter tube. Next, this was soaked in an aqueous solution (pH 8.0) containing 0.1% by weight of dibekacin sulfate (mfd. by Meiji Seika Kaisha) for 16 hours at room temperature and then washed with water. After washing, this was dried to prepare a medical device of the invention. When the antimicrobial activity and urokinase activity of the thus obtained catheter tube samples were examined by the methods of Reference Examples 1 and 3, it was confirmed that they possessed both of these activities.

These antimicrobial antithrombogenic catheter tube samples were soaked in physiological saline and shaken at 37° C. While changing physiological saline every day, the catheter tube samples were taken out periodically (on days 0 (before soaking), 7, 14, 21, 28, 56 and 84) and dried under a reduced pressure. Antimicrobial activity of the resulting catheter tubes was measured by the method of Reference Example 1. The results are shown in FIG. 1.

Examples 8 and 9

Medical devices of the invention were prepared by repeating the procedure of Example 7, except that the amount of polyethylene glycol was changed to 0.13% by weight (Example 8, terminal hydroxyl groups of polyethylene glycol: 0.5 mol % based on acid anhydride groups in the high molecular weight substance) and to 2.55% by weight (Example 9, terminal hydroxyl groups of polyethylene glycol: 10.0 mol % based on acid anhydride groups in the high molecular weight substance), respectively. When the antimicrobial activity and urokinase activity of the thus obtained catheter tube samples were evaluated by the methods of Reference Examples 1 and 3, it was confirmed that they possessed both of these activities.

After soaking these antimicrobial antithrombogenic catheter tube samples in physiological saline, the antimicrobial activity was measured periodically (on days 0, 7, 14, 21, 28, 56 and 84) in the same manner as described in Example 7. The results are shown in FIG. 1.

Comparative Examples 4 and 5

Catheter tube samples were prepared by repeating the procedure of Example 7, except that the amount of polyethylene glycol was changed to 0.07% by weight (Comparative Example 4, terminal hydroxyl groups of polyethylene glycol: 0.25 mol % based on acid anhydride groups in the high molecular weight substance) and to 5.1% by weight (Comparative Example 5, terminal hydroxyl groups of polyethylene glycol: 20.0 mol % based on acid anhydride groups in the high molecular weight substance), respectively. When the antimicrobial activity and urokinase activity of the thus obtained catheter tube samples were evaluated by the methods of Reference Examples 1 and 3, it was confirmed that they possessed both of these activities.

After soaking these antimicrobial antithrombogenic catheter tube samples in physiological saline, the antimicrobial activity was measured periodically (on days 0, 7, 14, 21, 28, 56 and 84) in the same manner as described in Example 1. The results are shown in FIG. 1.

Example 10

A polyurethane film for wound dressing use was soaked in a methyl ethyl ketone solution prepared by dissolving 2% by weight of a maleic anhydride-methyl vinyl ether copolymer having a molecular weight of about 67,000 (mfd. by I. S. P.; 429 moles maleic anhydride groups per 1 mole of the copolymer) and 0.102% by weight of poly(oxyethylene) diamine having a molecular weight of 400 (mfd. by Sanyo Chemical Industries; 2 moles amino groups per 1 mole of the copolymer) (terminal amino groups of poly(oxyethylene) diamine: 4.0 mol % based on acid anhydride groups in the maleic anhydride-methyl vinyl ether copolymer), for 1 hour at room temperature and then removed from the solution. The treated polyurethane film was allowed to stand at room temperature for 24 hours to be air-dried. After washing with methyl ethyl ketone and subsequent drying, this was soaked in a phosphate buffer solution (pH 7.0) containing 1,000 units/ml of urokinase (mfd. by Yoshitomi Pharmaceutical) and 0.1% by weight of vancomycin hydrochloride (mfd. by Nakalai Tesque) at 20° C. for 24 hours to prepare a medical device of the invention. When the antimicrobial activity and fibrinolytic activity of the thus obtained polyurethane film were evaluated by the methods of Reference Examples 1 and 2, it was confirmed that they possessed both of these activities. Samples of the thus obtained antimicrobial antithrombogenic polyurethane film were soaked in physiological saline and shaken at 37° C. While changing physiological saline every day, the polyurethane film samples were taken out at appropriate intervals and dried. Antimicrobial activity of the resulting films was measured by the method of Reference Example 1. Inhibition zones on the 0th, 7th, 14th and 28th days were 40 mm, 25 mm, 10 mm and 5 mm, respectively.

Examples 11 and 12

Polyurethane films were prepared by repeating the procedure of Example 10, except that the amount of poly (oxyethylene)diamine was changed to 0.013% by weight (Example 11, terminal amino groups of poly(oxyethylene) diamine: 0.5 mol % based on acid anhydride groups in the high molecular weight substance) and to 0.255% by weight (Example 12, terminal amino groups of poly(oxyethylene) diamine: 10.0 mol % based on acid anhydride groups in the high molecular weight substance), respectively. When the antimicrobial activity and fibrinolytic activity of the thus obtained films were evaluated by the methods of Reference Examples 1 and 2, it was confirmed that they possessed both of these activities.

After soaking samples of these antimicrobial antithrombogenic polyurethane films in physiological saline, the antimicrobial activity was measured periodically (on days 0, 7, 14 and 28) in the same manner as described in Example 10. Inhibition zones of the samples of both Examples 11 and 12 on the 0th, 7th, 14th and 28th days were 40 mm, 20 mm, 8 mm and 3 mm, respectively.

Comparative Examples 6 and 7

Polyurethane films were prepared by repeating the procedure of Example 10, except that the amount of poly(oxyethylene)diamine was changed to 0.007% by weight (Comparative Example 6, terminal amino groups of poly(oxyethylene)diamine: 0.25 mol % based on acid anhydride groups in the high molecular weight substance) and to 0.51% by weight (Comparative Example 7, terminal amino groups of poly(oxyethylene)diamine: 20.0 mol % based on acid anhydride groups in the high molecular weight substance), respectively. When the antimicrobial activity and fibrinolytic activity of the thus obtained films were evaluated by the methods of Reference Examples 1 and 2, it was confirmed that they possessed both of these activities.

After soaking samples of these antimicrobial antithrombogenic polyurethane films in physiological saline, the antimicrobial activity was measured periodically (on days 0, 7, 14 and 28) in the same manner as described in Example 10. Inhibition zones of the samples of Comparative Examples 6 and 7 on the 0th day were 40 mm and 39 mm, respectively, and inhibition zones of the samples on the 7th day were 5 mm and 4 mm, respectively, but no inhibition zone was formed by the samples on and after the 14th day of soaking.

Effect of the Invention

According to the invention, a medical device having both a physiologically active function and an antimicrobial function can be obtained by a convenient method independent of the kind of base material. Since an antimicrobial substance bonded to a cross-linked coating film formed on its surface is gradually released under physiological indwelling conditions, this medical device can retain antimicrobial activity for a prolonged period of time.

This application is based on Japanese patent application No. Hei.-9-146220, filed Jun. 4, 1997, herein incorporated by reference.

While the invention has been described in detail and with reference to specific examples thereof, it will be apparent to one skilled in the art that various changes and modifications can be made therein without departing from the spirit and scope thereof.

What is claimed is:

1. An antimicrobial medical device having physiological activity, which comprises a cross-linked coating film constituting a high molecular weight substance having acid anhydride groups formed on a surface of a base material, said cross-linked coating film is prepared by reacting from 0.5 to 10 mol % of the acid anhydride groups contained in the high molecular weight substance with a compound having two or more active hydrogen atoms in one molecule, and wherein a physiologically active substance and an antimicrobial substance are bonded to the cross-linked coating film.

2. The antimicrobial medical device of claim 1, wherein said antimicrobial substance is ionically bonded to the cross-linked coating film.

3. The antimicrobial medical device of claim 1, wherein said physiologically active substance is covalently bonded to the cross-linked coating film.

4. The antimicrobial medical device of claim 1, wherein said medical device is adapted for indwelling in a living body.

5. The antimicrobial medical device of claim 4, wherein said medical device is selected from the group consisting of a catheter, an artificial blood vessel, a shunt tube, a canula, a dilator, an indwelling needle, a guide wire, a sensor, a tracheotomy tube, an endotracheal tube, a feeding tube, an artificial kidney, an artificial heart, an artificial valve and an artificial lung.

6. The antimicrobial medical device of claim 1, wherein the high molecular weight substance is a polymer or copolymer comprising repeating units each having an acid anhydride group.

7. The anitmicrobial medical device of claim 1, wherein said high molecular weight substance having acid anhydride groups is selected from the group consisting of maleic anhydride polymers and copolymers, acrylic anhydride polymers and copolymers and methacrylic anhydride polymers and copolymers.

8. The anitmicrobial medical device of claim 1, wherein said high molecular weight substance having acid anhydride groups has a molecular weight of 500 or more.

9. The antimicrobial medical device of claim 1, wherein said compound having two or more active hydrogen atoms in one molecule is selected from the group consisting of polyols and polyamines.

10. The antimicrobial medical device of claim 1, wherein said physiologically active substance comprises a fibrinolytic enzyme.

11. The antimicrobial medical device of claim 1, wherein said high molecular weight substance having acid anhydride groups comprises maleic anhydride-methyl vinyl ether copolymer, said compound having two or more active hydrogen atoms in one molecule comprises polyethylene glycol, and said cross-linked coating film is prepared by reacting about 4.0 mol % of the acid anhydride groups contained in the high molecular weight substance with the compound having two or more active hydrogen atoms in one molecule.

12. The antimicrobial medical device of claim 11, wherein said physiologically active substance comprises urokinase and said antimicrobial substance comprises dibekacin sulfate.

13. The antimicrobial medical device of claim 11, wherein said physiologically active substance comprises urokinase and said antimicrobial substance comprises an aminoglycoside antibacterial drug.

14. The antimicrobial medical device of claim 1, wherein said high molecular weight substance having acid anhydride groups comprises maleic anhydride-methyl vinyl ether copolymer, said compound having two or more active hydrogen atoms in one molecule comprises polyethylene glycol, and said cross-linked coating film is prepared by reacting 0.5 mol % of the acid anhydride groups contained in the high molecular weight substance with the compound having two or more active hydrogen atoms in one molecule.

15. The antimicrobial medical device of claim 1, wherein said high molecular weight substance having acid anhydride groups comprises maleic anhydride-methyl vinyl ether copolymer, said compound having two or more active hydrogen atoms in one molecule comprises polyethylene glycol, and said cross-linked coating film is prepared by reacting 10.0 mol % of the acid anhydride groups contained in the high molecular weight substance with the compound having two or more active hydrogen atoms in one molecule.

16. The antimicrobial medical device of claim 1, wherein said high molecular weight substance having acid anhydride groups comprises maleic anhydride-methyl vinyl ether copolymer, said compound having two or more active hydrogen atoms in one molecule comprises poly(oxyethylene)diamine, and said cross-linked coating film is prepared by reacting about 4.0 mol % of the acid anhydride groups contained in the high molecular weight substance with the compound having two or more active hydrogen atoms in one molecule.

17. The antimicrobial medical device of claim 16, wherein said physiologically active substance comprises urokinase and said antimicrobial substance comprises vancomycin.

18. The antimicrobial medical device of claim 1, wherein said base material comprises a polyurethane film for wound dressing.

19. A method for producing an antimicrobial medical device having physiological activity, which comprises forming a cross-linked coating film constituting a high molecular weight substance having acid anhydride groups formed on a surface of a base material, by reacting from 0.5 to 10 mol % of the acid anhydride groups contained in the high molecular weight substance with a compound having two or more active hydrogen atoms in one molecule, and subsequently bonding a physiologically active substance and an antimicrobial substance to the cross-linked coating film.

20. The method of claim 19, which comprises contacting the base material with a solution of the high molecular weight substance having acid anhydride groups and the compound having two or more active hydrogen atoms in one molecule.

* * * * *